US006673626B1

(12) United States Patent
Rabinovich et al.

(10) Patent No.: US 6,673,626 B1
(45) Date of Patent: Jan. 6, 2004

(54) OPTOELECTRONIC CIRCUIT FOR DETECTING CHANGES IN FLUORESCENCE LIFETIME

(75) Inventors: Emmanuel Rabinovich, Albuquerque, NM (US); Michael J. O'Brien, Albuquerque, NM (US); Gabriel P. Lopez, Albuquerque, NM (US)

(73) Assignee: Science & Technology Corporation University of New Mexico, Albuquerque, NM (US)

( * ) Notice: Subject to any disclaimer, the term of this patent is extended or adjusted under 35 U.S.C. 154(b) by 246 days.

(21) Appl. No.: 10/004,416

(22) Filed: Oct. 31, 2001

Related U.S. Application Data

(60) Provisional application No. 60/244,813, filed on Oct. 31, 2000.

(51) Int. Cl.[7] ................................................ G01N 21/64
(52) U.S. Cl. ................. 436/172; 422/82.08; 250/458.1; 250/459.1
(58) Field of Search ............................ 422/82.06, 82.07, 422/82.08, 82.11; 436/172; 250/458.1, 459.1

(56) References Cited

U.S. PATENT DOCUMENTS

| | | | |
|---|---|---|---|
| 4,410,992 A | 10/1983 | Javan | |
| 4,468,776 A | 8/1984 | McLellan | |
| 4,713,540 A | 12/1987 | Gilby et al. | |
| 5,196,903 A | 3/1993 | Masutani | |
| 5,257,202 A * | 10/1993 | Feddersen et al. ............. 702/32 |
| 5,262,644 A | 11/1993 | Maguire | |
| 5,315,993 A | 5/1994 | Alcala | |
| 5,323,010 A | 6/1994 | Gratton et al. | |
| 5,504,337 A * | 4/1996 | Lakowicz et al. ....... 250/461.2 |
| 5,545,517 A | 8/1996 | Thompson | |
| 5,559,358 A | 9/1996 | Burns et al. | |
| 5,818,582 A * | 10/1998 | Fernandez et al. .......... 356/318 |
| 5,828,452 A | 10/1998 | Gillispie et al. | |
| 5,856,869 A | 1/1999 | Cooper et al. | |
| 5,946,090 A | 8/1999 | Tashiro et al. | |
| 5,981,957 A * | 11/1999 | Cruce et al. ............. 250/458.1 |
| 6,038,041 A | 3/2000 | Poon et al. | |
| 6,157,037 A | 12/2000 | Danielson | |
| 6,160,826 A | 12/2000 | Swanson et al. | |
| 6,323,495 B1 * | 11/2001 | Riedel ..................... 250/458.1 |
| 6,426,505 B1 * | 7/2002 | Rao et al. ................ 250/458.1 |

OTHER PUBLICATIONS

Bambot, S.B., et al., "Phase Fluorometirc Sterilizable Optical Oxygen Sensor," *Biotech and Bioeng*, vol. 43, pp 1139–1145 (1994).

Gustafsson, U., et al., "Frequency–Modulation Spectroscopy with Blue Diode Lasers," *Applied Optics*, vol. 39, No. 21, pp 3774–3780 (Jul. 20, 2000).

O'Brien, M.J., et al., "Technique for Detecting Changes in Fluorescence Lifetime by Means of Optoelectronic Circuit Auto–Oscillation," *Optics Letters*, vol. 26, No. 16, pp 1256–1258 (Aug. 15 2001).

O'Brien, M.J., et al., "Optoelectronic Closed Looop Auto–Oscillator for Fluorescence Lifetime Detection: a New Fluorimetry Technique with Applications to Chemical/Biosensors," *Proc. SPIE 4263*, pp 170–177 (2001).

(List continued on next page.)

*Primary Examiner*—Jeffrey Snay
(74) *Attorney, Agent, or Firm*—Jeffrey D. Myers

(57) ABSTRACT

A fluorescence average excited-state lifetime sensor and sensing method comprising a fluorescence excitation light source, light-directing apparatus directing light from the light source to a sample, light-receiving apparatus receiving fluorescence light generated by the sample, and a narrow-band resonance amplifier providing gain necessary to support self-oscillations in an opto-electronic loop comprising the light source, the sample, the light-directing apparatus, the light-receiving apparatus, and the resonance amplifier.

59 Claims, 5 Drawing Sheets

OTHER PUBLICATIONS

Nakazawa, M., et al., "An Optoelectornic Self–Oscillatory Circuit with an Optical Fiber Delayed Feedback and its Injection Locking Technique," *J of Lightwave Technology*, vol. LT–2, No. 5, pp 719–730 (Oct. 1984).

Rabinovich, E.M., et al., "Remote Vibration Sensing Using a Radio–Frequency Auto–Oscillatory Opto–Electronic Circuit with Fibre–Optical Delay Line," *Meas. Sci. Technol.*, vol. 6, p 1407–1412 (1995).

Rabinovich, E., et al., "Phase–Sensitive Multichannel Detection System for Chemical and Biosensor Arrays and Fluorescence Lifetime–Based Imaging," *Rev of Sci Instr.*, vol. 71, No. 2, pp 522–529 (Feb. 2000).

Sekar, M.M.A., et al., "Multifunctional Monolayer Assemblies for Reversible Direct Flurorescence Transduction of Protein—Ligand Interactions at Surfaces," *J. Am. Chem. Soc.*, vol. 131, pp 5137–5141 (1999).

Swift, K., et al., "Dual Laser Flurorescence Correlation Spectroscopy as a Biophysical Probe of Binding Interactions," *as published in Proc. SPIE 4252*, pp 47–58 (2001).

Szmacinski, H., et al., "Flurorescence Lifetime–Based Sensing and Imaging," *Sensors and Actuators*, vol. B 29, pp 16–24 (1995).

* cited by examiner

OPTOELECTRONIC CIRCUIT FOR DETECTING CHANGES IN FLUORESCENCE LIFETIME

CROSS-REFERENCE TO RELATED APPLICATIONS

This application claims the benefit of the filing of U.S. Provisional Patent Application Ser. No. 60/244,813, entitled "New Method of Modulation Spectroscopy for Measurements of Changes in Excited State Lifetime", filed on Oct. 31, 2000, and the specification thereof is incorporated herein by reference.

GOVERNMENT RIGHTS

The U.S. Government has a paid-up license in this invention and the right in limited circumstances to require the patent owner to license others on reasonable terms as provided for by the terms of Contract No. N00014-95-1315 awarded by the U.S. Office of Naval Research.

BACKGROUND OF THE INVENTION

1. Field of the Invention (Technical Field)

The present invention relates to fluorescence sensing systems employing excited-state lifetime detection for use, for example, in chemical and biological sensors.

2. Background Art

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

Designers of chemical and biological sensors often choose fluorescence as their detection modality because it offers high sensitivity and a large choice of fluorescence sensor transduction techniques. M. Sekar, et al., J. Am. Chem. Soc. 121, 5135–5141 (1999). Sensor systems that utilize some form of excited-state lifetime detection have several advantages over those that use simple intensity detection. Most of these benefits are in the form of reduced sensitivity to undesirable effects, including changes in excitation light intensity and in dye concentration, fluorophore bleaching, and sample turbidity. E. Rabinovich, et al., Rev. Sci. Instrum. 71, 522–529 (2000); H. Szmancinski, et al., Sens. Actuators B 29, 16–24 (1995).

There are two well-developed classes of excited-state lifetime detection techniques. Time-domain methods rely on direct measurements of fluorescence intensity decay. Frequency-domain methods (e.g., modulation spectroscopy) measure the effects of finite fluorescence lifetimes on the sinusoidal intensity modulation of fluorescence emission, typically the effects on modulation depth and (or) modulation phase shifts. H. Szmancinski, et al., supra.

The present invention is based on modulation spectroscopy. Changes in fluorescence lifetime alter the frequency of auto-oscillations in a closed-loop optoelectronic circuit. The oscillation exists as a radio frequency (RF) sinusoidal modulation of the fluorescence excitation and emission intensity. This technique is relatively straightforward to implement and is inexpensive. It has high sensitivity over a broad range of lifetimes because a wide range of frequencies may be measured precisely.

SUMMARY OF THE INVENTION (DISCLOSURE OF THE INVENTION)

The present invention is of a fluorescence average excited-state lifetime sensor comprising: a fluorescence excitation light source; light-directing apparatus directing light from the light source to a sample; light-receiving apparatus receiving fluorescence light generated by the sample; and a narrow-band resonance amplifier providing gain necessary to support self-oscillations in an opto-electronic loop comprising the light source, the sample, the light-directing apparatus, the light-receiving apparatus, and the resonance amplifier. In the preferred embodiment, light from the light source and the fluorescence light have different wavelengths and each carry a radio frequency intensity modulation in the loop. The light source can be a light emitting diode (e.g., blue). The light-receiving apparatus preferably comprises a long-wavelength-pass optical filter to prevent reception of light from the light source. The light-directing apparatus preferably directs light to a plurality of fluorophores, and the light-receiving apparatus receives light with radio frequency intensity modulation of identical frequency as that of the light source but phase shifted. The light-receiving apparatus preferably comprises a photomultiplier tube, with the light-receiving apparatus connected to an input of the resonance amplifier. The amplifier preferably comprises a resonance radio frequency amplifier, preferably with the central frequency of the amplifier and lengths of the light-directing and light-receiving apparatus being such that the RF modulation frequency multiplied by the excited-state fluorescence lifetime of fluorophores in the sample is approximately one. The sensor preferably comprises a frequency counter receiving a signal between the amplifier and the light source, as well as a second light source and a photodetector receiving output from the second light source and providing input to the frequency counter. The light source can be a diode laser (e.g., blue or red). The resonance amplifier preferably prevents higher order oscillations. An alternative embodiment adds an electronic phase shifter within the opto-electronic loop and also a second opto-electronic loop comprising the electronic phase shifter, a second apparatus for receiving fluorescence light generated by the sample, and a phase detector. In that embodiment, light from the light source is used as a light carrier of radio frequency intensity modulation in the first opto-electronic loop, and the fluorescence light is used as a light carrier of radio frequency intensity modulation in the second opto-electronic loop. The sensor preferably has a sub-picosecond resolution for changes in average excited-state lifetime of the sample. The sensor can measure changes of chemical environment when the sample exhibits changes of fluorescence average excited-state lifetime in response to changes of the chemical environment, changes of physical environment when the sample exhibits changes of fluorescence average excited-state lifetime in response to changes of the physical environment, changes of concentration of one or more chemical species when the sample exhibits changes of fluorescence average excited-state lifetime in response to changes of concentration of the chemical species, and changes of concentration of one or more biological species when the sample exhibits changes of fluorescence average excited-state lifetime in response to changes of concentration of the biological species.

The invention is also of a fluorescence average absolute lifetime sensor comprising: a fluorescence excitation light source; light-directing apparatus directing light from the light source to a sample; light-receiving apparatus receiving fluorescence light generated by the sample; an electronic phase shifter; and a narrow-band resonance amplifier providing gain necessary to support self-oscillations in an opto-electronic loop comprising the light source, the sample, the light-directing apparatus, the light-receiving apparatus, the phase shifter, and the resonance amplifier. In the preferred embodiment, light from the light source and the fluorescence light have different wavelengths and each carry a radio frequency intensity modulation in the loop. The amplifier is preferably a resonance radio frequency amplifier, with the central frequency of the amplifier and lengths of the light-directing and light-receiving apparatus being such that an RF modulation frequency multiplied by an excited-state fluorescence lifetime of fluorophores in the sample is not approximately one. The light-directing apparatus preferably directs light to a plurality of fluorophores, with the light-receiving apparatus receiving light with radio frequency intensity modulation of identical frequency as that of the light source but phase shifted.

The invention is additionally of a fluorescence average excited-state lifetime sensing method comprising: exciting a fluorescence excitation light source; directing light from the light source to a sample; receiving fluorescence light generated by the sample; and providing narrow-band resonance amplification providing gain necessary to support self-oscillations in an opto-electronic loop comprising the light source, the sample, light directing apparatus, light receiving apparatus, and resonance amplification apparatus. In the preferred embodiment, the light source and the fluorescence light have different wavelengths and each carry a radio frequency intensity modulation in the loop. The light source can be a light emitting diode (e.g., blue). In the receiving step, a long-wavelength-pass optical filter is preferably employed to prevent reception of light from the light source. The directing step preferably directs light to a plurality of fluorophores, and the receiving step receives light with radio frequency intensity modulation of identical frequency as that of the light source but phase shifted. Receiving is preferably done by photodetector, such as a photomultiplier tube. In the receiving and providing steps, the photodetector is preferably connected to an input of the resonance amplification apparatus, which is preferably a resonance radio frequency amplifier, most preferably with a central frequency of the amplifier and lengths of the light directing and receiving apparatus being such that an RF modulation frequency multiplied by an excited-state fluorescence lifetime of fluorophores in the sample is approximately one. A frequency counter is preferably employed to receive a signal between the amplifier and the light source, together with a second light source and a photodetector receiving output from the second light source and providing input to the frequency counter. The light source may be a diode laser (e.g., blue or red). The resonance amplification preferably prevents higher order oscillations. In an alternative embodiment, an electronic phase shifter is employed within the opto-electronic loop and a second opto-electronic loop is employed comprising the electronic phase shifter, a second apparatus for receiving fluorescence light generated by the sample, and a phase detector. The method preferably provides a sub-picosecond resolution for changes in average excited-state lifetime of the sample. The method can measure changes of chemical environment when the sample exhibits changes of fluorescence average excited-state lifetime in response to changes of the chemical environment, changes of physical environment when the sample exhibits changes of fluorescence average excited-state lifetime in response to changes of the physical environment, changes of concentration of one or more chemical species when the sample exhibits changes of fluorescence average excited-state lifetime in response to changes of concentration of the chemical species, and changes of concentration of one or more biological species when the sample exhibits changes of fluorescence average excited-state lifetime in response to changes of concentration of the biological species. The method can obtain directly information regarding changes of concentration in a species selected from the group consisting of chemical and biological species from measurement of self-oscillation frequency in the opto-electronic loop.

The invention is further of a fluorescence average absolute lifetime sensing method comprising: exciting a fluorescence excitation light source; directing light from the light source to a sample; receiving fluorescence light generated by the sample; employing an electronic phase shifter; and providing narrow-band resonance amplification providing gain necessary to support self-oscillations in an opto-electronic loop comprising the light source, the sample, light directing apparatus, light receiving apparatus, the phase shifter, and resonance amplification apparatus. In the preferred embodiment, the providing step employs a resonance radio frequency amplifier, preferably with a central frequency of the amplifier and lengths of the light directing and receiving apparatus being such that an RF modulation frequency multiplied by an excited-state fluorescence lifetime of fluorophores in the sample is not approximately one. The directing step preferably directs light to a plurality of fluorophores, with the receiving step receiving light with radio frequency intensity modulation of identical frequency as that of the light source but phase shifted.

Objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

Figure 1:
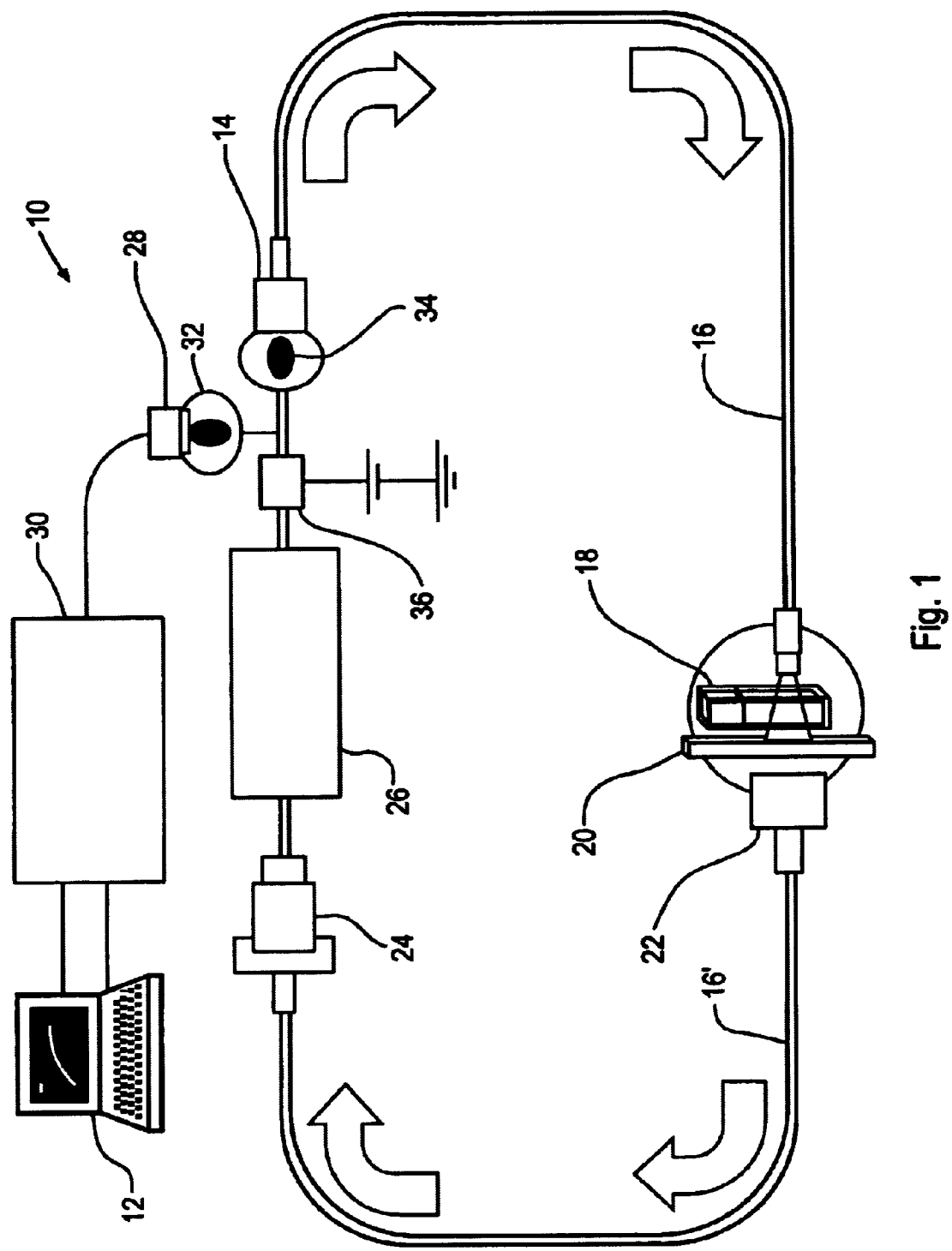
FIG. 1 is a block diagram of the preferred apparatus of the invention for average excited-state lifetime measurements.

DESCRIPTION OF THE PREFERRED EMBODIMENTS (BEST MODES FOR CARRYING OUT THE INVENTION)

The present invention is of a direct, inexpensive, and highly precise system and method for average excited-state fluorescence-lifetime-based measurement. The preferred detection system of the invention comprises a closed-loop optoelectronic device preferably comprising a radio frequency resonance amplifier, a fluorescence excitation light source, a fiber-optic delay line, and a photodetector. The invention exhibits auto-oscillations in the form of intensity modulation. The oscillation frequency varies with the modulation phase shift of the fluorescent light. This frequency is used as the detection parameter. The invention is well suited for chemical and biosensor applications. Not that the present invention is not designed to resolve the individual lifetime components of multiexponential decay rates, but rather to usefully employ average excited-state fluorescence lifetime measurements.

The principles behind closed-loop auto-oscillation devices are straightforward. If the output of an amplifier is returned to its input with positive feedback, such that the returned signal is in phase with the amplifier output, the circuit will begin to oscillate as the gain of the amplifier increases to equal the signal losses in the circuit. This phenomenon is the foundation of many oscillators, including lasers. Optoelectronic auto-oscillating systems with fiberoptic delay lines have been developed by others. M. Nakazawa, et al., J. Lightwave Technol. 2, 719–729 (1984); T. V. Babkina, et al., Telecommun. Radio Eng. 46, 118–121 (1991). A remote vibration sensor with a closed-loop system has been created. E. M. Rabinovich, et al., Meas. Sci. Technol. 6, 1407–1412 (1995). However, the present invention is believed to be the first application of fluorescence as a phase-shifting mechanism inside a closed-loop system and the first closed-loop system to use modulation light carriers of two different optical wavelengths (fluorescence excitation and emission light) within the same loop. M. J. O'Brien, et al., *Proc. SPIE* 4263, 170–177 (2001).

Closed-loop, auto-oscillatory systems typically consist of a light source, a fiber-optic delay line, a photodetector, and an amplifier with a narrow gain envelope in the RF regime. Provided that the round-trip signal gains and losses are equal (gain condition), the system will exhibit auto-oscillations in the form of sinusoidal intensity modulation that satisfy the phase-matching condition $$(nL/c)\Omega + \Phi = 2\pi N, \quad (1)$$

where n is the effective refractive index of the fiber delay line, L is the length of the optical delay fiber, c is the speed of light in vacuum, $\Omega$ is the modulation frequency (in radians/second), $\Phi$ represents the sum of all discrete phase shifts in the loop, and N is any integer. The modulation frequency depends on the phase delay of the feedback loop. It should be emphasized that the frequencies, wavelengths, and phase shifts of the light itself are irrelevant. Only the frequencies and phase shifts of the RF modulation appear in Eq. 1.

The modulation phase shift produced by a fluorophore is $\Phi_f = \arctan(\Omega\tau)$ for single exponential decay (where $\tau$ is the fluorescence lifetime). E. Rabinovich, et al. (2000), supra. Assuming that $\Phi = \Phi_f + \Phi_K$, where $\Phi_K$ is a constant that represents the net phase shifts of the loop from the optoelectronics (including those that have negligible phase responses to changes in frequency, such as the resonance amplifier), and using Eq. 1, one may obtain the following relationship between small lifetime changes and small frequency shifts:

$$\Delta\Omega = -\left[\frac{g(\Omega\tau)}{(nL/c) + g(\Omega\tau)/\Omega}\right]\frac{\Delta\tau}{\tau}, \quad (2)$$

where $g(\Omega\tau) \equiv (\Omega\tau)/(1+(\Omega\tau)^2)$. Fluorophores will exhibit maximum phase shifts for given changes in lifetime, E. Rabinovich, et al. (2000), supra, for $\Omega\tau \approx 1$. As one would expect, the bracketed part of Eq. 2 also has a maximum in this regime, and this maximum defines the optimal $\Omega$. Eq. 2 then simplifies to $$\Delta\Omega = -\left[\frac{1/2}{nL/c + 1/(2\Omega)}\right]\frac{\Delta\tau}{\tau}. \quad (3)$$

For testing purposes the fluorescent dye carboxy seminaphthofluorescein (SNAFL-2) was chosen from Molecular Probes, Inc. See http://www.probes.com. Changes in the pH of a solution that contains this dye cause substantial lifetime changes, E. Rabinovich, et al. (2000), supra, leading to large modulation-signal phase shifts, which produce good frequency responses. An aqueous SNAFL-2 solution with a pH of 9.2 was placed in a cuvette 18 located within the gap between the two parts of the optical delay line, along with a low-pass (long-wavelength) optical filter 20 to prevent the excitation light from entering the second part of the loop (as shown in FIG. 1). The lifetime of SNAFL-2 at this pH is 3.2 ns. E. Rabinovich, et al. (2000), supra. 0.1-nM solutions of NaOH and HCl were prepared to alter the pH of the dye solution during the experiment.

A schematic of the preferred closed-loop auto-oscillating detection system 10 is shown in FIG. 1. The system comprises a resonance RF amplifier 26 (e.g., RTA-4-4505 RF amplifier, Radar Technology Inc.; central frequency, $\approx 45$ MHz; bandwidth, $\approx 5$ MHz), a fluorescence excitation light source 34 (e.g., blue LED NSPB500S, Nichia America Corporation), two pieces of multimode fiber 16,16' (e.g., with total length, 8.8 m, with 600-mm core diameter; Thor Labs, Inc.), two fiber-optic light collimators 14,22, and a photomultiplier tube 24 (PMT) (e.g., ultracompact Model 5600 PMT, Hamamatsu Corporation). A dc offset module is preferably connected to the LED. The fiber length and the central frequency of the amplifier are preferably selected to meet the condition $\Omega\tau \approx 1$ for the above solution.

The RF signal is preferably extracted from the loop into an analyzing personal computer 12 (or other computing platform or other frequency analyzing device) in either of two ways. The first is a direct electrical connection to the closed loop with a coaxial cable attached to a T junction 36 in the loop and connected to the frequency counter 30 (e.g., HP5328A, Hewlett-Packard, Inc.). This direct connection can affect the circuit because of the capacitance of the cabling and the input impedance of the frequency-counting circuitry. The noninvasive alternative uses an optoelectronic (optron) interface comprising a second light source 32 connected to the loop and a second photodetector 28 connected to the frequency-counting device. The noninvasive technique is preferred because it leads to better stability.

The gain may be adjusted to obtain stable, sinusoidal auto-oscillations (which can be visually monitored with an oscilloscope and a spectrum analyzer). The initial signal changes after addition of several drops of acid solution. To illustrate the reverse effect, several drops of base solution were also added.

Figure 2:
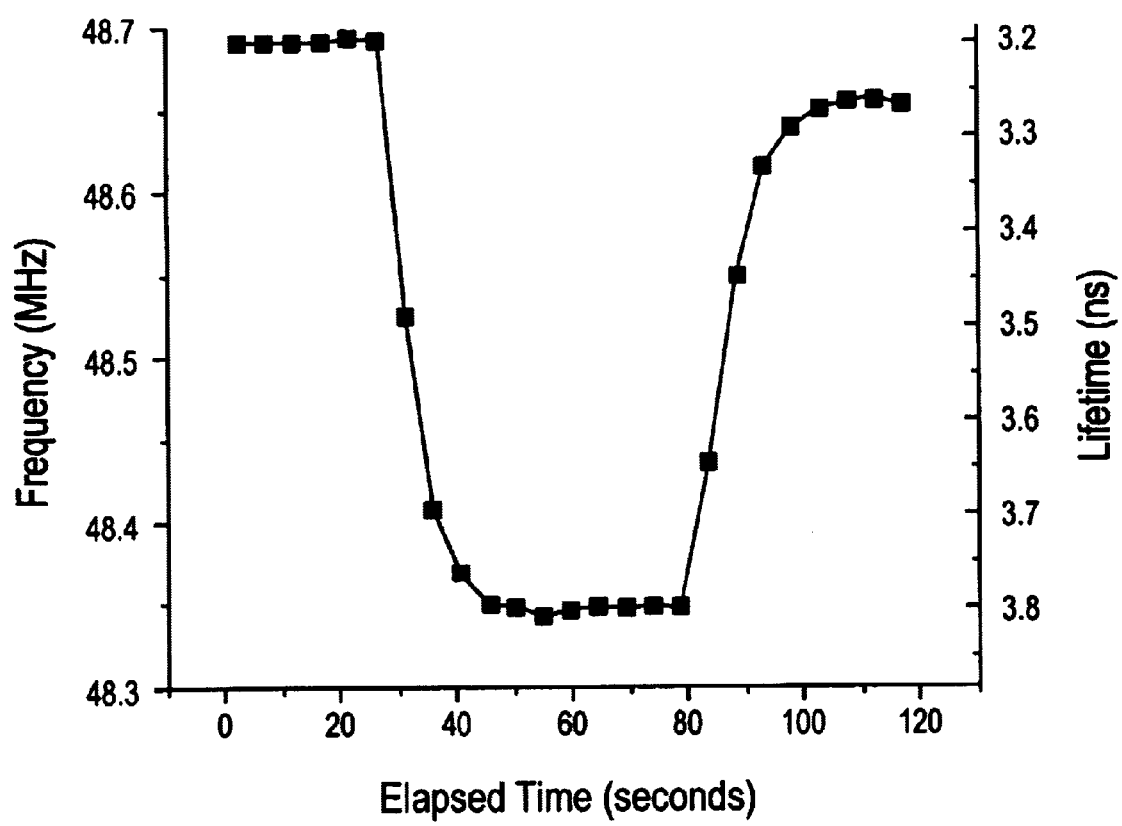
FIG. 2 is a graph of experimental data at 16×averaging; the lifetime axis was estimated with Eq. 3 and the known lifetime for the SNAFL solution at pH 9.2.

The results, with 16×averaging (each set of 16 consecutive measurements in the series averaged into one data point after the experiment), are shown in FIG. 2. The noninstantaneous signal response to the introduction of acid and base is due to mixing times. Noise levels (determined by the standard deviation of data points acquired during the first 15 s of data acquisition) for 1×, 4×, and 16×averaging are, respectively, 970, 560, and 130 Hz. Using Eq. (3), one can estimate the lifetime resolutions at approximately 1.7, 1, and 0.2 ps for the three averaging levels. The variation from the typical $N^{-\frac{1}{2}}$ noise reduction at higher averaging levels may be due to a non-Gaussian noise distribution.

Removal of the cuvette and the low-pass filter reduced the signal losses in the circuit by approximately 10 dB. When the circuit was oscillating under these conditions, the noise level was approximately 100 Hz (without any averaging). This noise is due to the optoelectronics of the circuit and may be considered the noise limit of the prototype (the frequency counter itself was observed to have 1-Hz stability when it was monitoring a 45-MHz signal from a digital signal generator).

The present invention provides a new and practical method of and system for modulation spectroscopy that is useful for measuring changes in fluorescence lifetime. It is simple and inexpensive and yields high-precision measurements. This system is ideally suited for biological and chemical sensor applications wherein relative measurements are sufficient. E. Rabinovich, et al. (2000), supra. Thus it is an attractive alternative to single-frequency phase fluorimeters. E. Rabinovich, et al. (2000), supra; H. Szmancinski, et al., supra; and S. B. Bambot, et al., Biotech. Bioeng. 43, 1139–1145 (1994). Whereas a single-frequency phase fluorimeter with 0.1° phase accuracy (twice better than typical, H. Szmancinski, et al., supra) has comparable data acquisition rates, it has only 5-ps lifetime resolution. E. Rabinovich, et al. (2000), supra.

The present invention is well suited for fluorophores with exited-state lifetimes with values of nanoseconds, which correspond to preferred modulation frequencies in the RF regime. A lifetime of the order of microseconds would require delay line lengths of the order of kilometers, leading to significant signal losses for visible (or ultraviolet) light. However, lifetimes shorter than nanoseconds are measurable. For example, a system constructed with a 1-GHz resonance frequency would be ideal for fluorophores with lifetimes of ~160 ps. Such a higher-frequency system requires an excitation light source that is capable of supporting the higher modulation frequencies, such as a diode laser. Frequencies in this regime have been used in modulation spectroscopy with blue diode lasers. U. Gustafsson, et al., Appl. Opt. 39, 3774–3780 (2000). Red laser diodes, for which several fluorescent dyes are available, K. Swift, et al., Proc. SPIE 4252, 47–58 (2001), have already been used for frequency-domain measurements with modulation frequencies as high as 2 GHz. H. Szmancinski, et al., supra. Laser diodes also offer superior modulation depth, reducing one source of signal loss in the circuit.

The optical design of the embodiment described above is not optimized in terms of losses. It couples only a fraction of the LED output into the fiber delay line. Much of the fluorescent light is similarly lost when it is coupled into the second part of the delay line. Use of pigtailed diode lasers and an integration sphere for collecting fluorescence, for example, would eliminate many of these losses. Removing losses from the optoelectronic circuit allows one to increase other losses (from low fluorescence efficiency, for example) and still make precise measurements.

Figure 4:
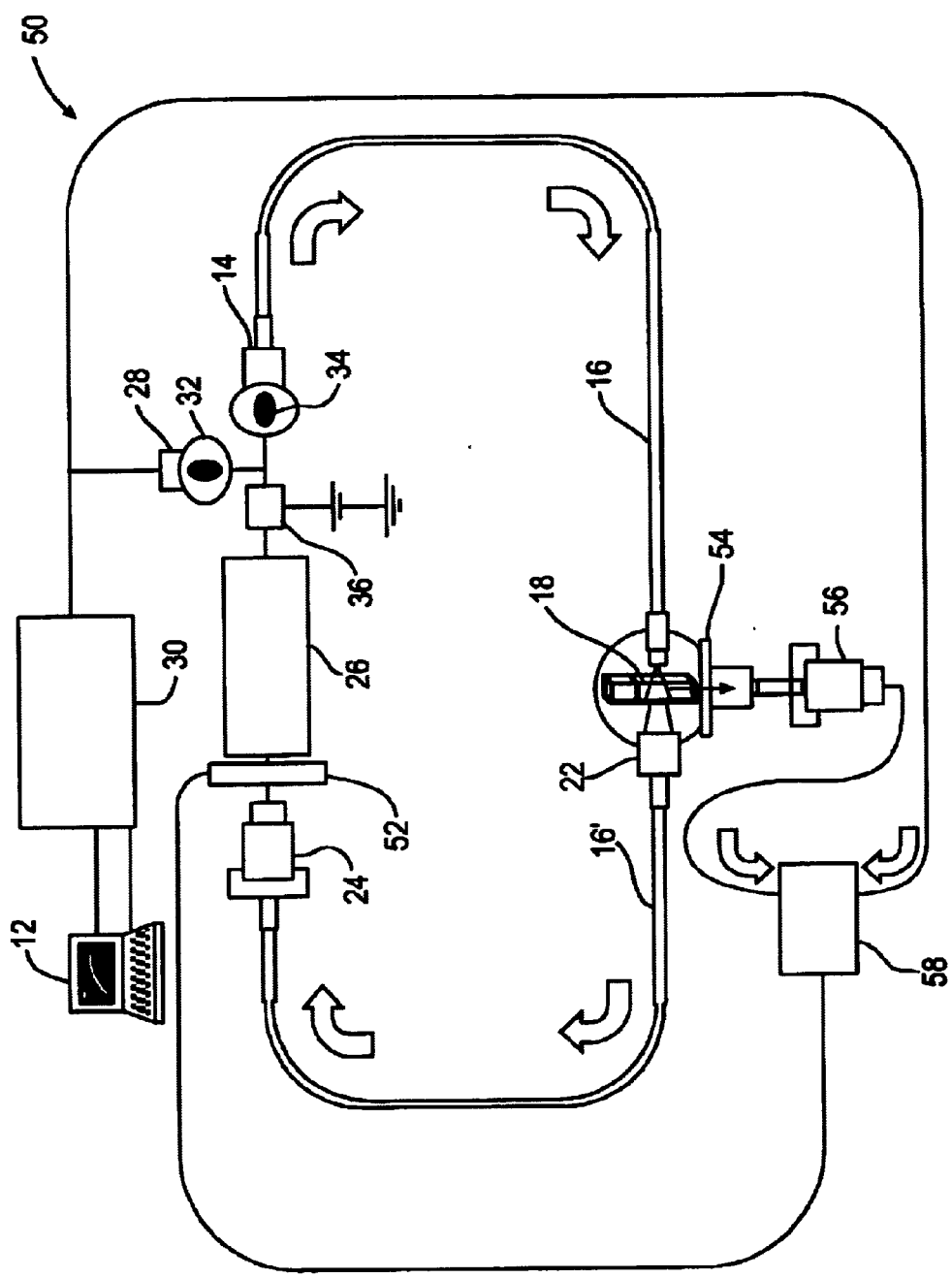
FIG. 4 is a block diagram of an alternative embodiment of the invention for average excited-state lifetime measurements which is particularly suited for low fluorescence efficiency.

An alternative embodiment 50 is shown in FIG. 4. In this variation, the excitation light is used as the carrier of the RF wave throughout the entire closed loop. There is no long-wavelength-pass filter to prevent the excitation light from entering the second part of the closed loop. The advantage of this is in the reduction of signal losses from the loop. In the preferred embodiment, any excitation light which is not converted into fluorescence is lost, and since the fluorescent light is not well directed, only a small part of it can be inserted into the second half of the loop. In the preferred embodiment, these losses must be compensated for by increasing the gain of the amplifier. High gain will typically accompany increased noise.

In this alternative embodiment, these sources of loss are removed, so the gain of the amplifier does not need to be so high to support self-oscillations. However, a different mechanism for detecting changes in lifetime is needed. It is preferred to use a second detector 56 along with a long-wavelength-pass filter 54 to detect the fluorescent light. The phase shift of the fluorescent light is converted into a DC electrical voltage by an electronic phase detector 58. This voltage is then fed into an electronic phase shifter 52 in the loop. A change in fluorescence lifetime results in a change in the phase shift of the RF signal of the fluorescent light. This, in turn, alters the voltage applied to the electronic phase shifter, resulting in a change in the self oscillation frequency of the loop until an equilibrium is reached.

Figure 3:
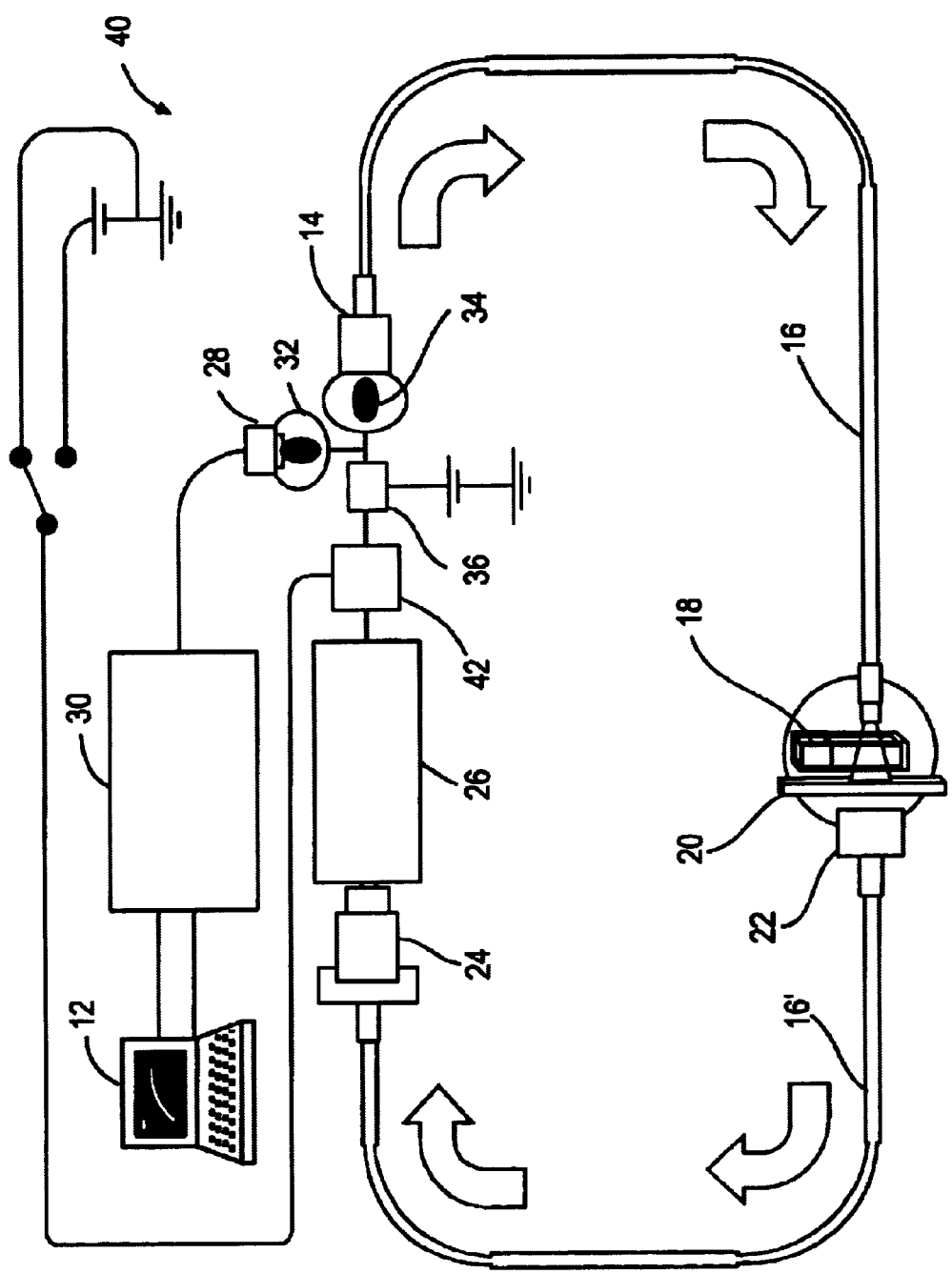
FIG. 3 is a block diagram of the apparatus of the invention for average absolute lifetime measurements.

In the preferred embodiment, absolute lifetime measurements are only possible with rigorous calibration methods to determine $\Phi_K$. A closed loop system 40 of the invention may also be used for simple absolute average lifetime measurements, which are not dependent upon $\Phi_k$. By inserting an electronic phase shifter 42 inside the closed loop as shown in FIG. 3, one can introduce a known $d\Phi$ into the loop. This will result in a frequency shift $d\Omega$. The ratio of the shifts, ($d\Phi d\Omega$) is dependent on the lifetime of the fluorophore, and can be used to determine the absolute value of the lifetime, with no dependence on other phase constants in the loop.

One starts with the phase matching condition for the loop:

$$\left(\frac{nl}{c}\right)\Omega + \Phi + \arctan(\Omega\tau) = 2\pi N \quad (4)$$

where $\Omega$ is the frequency of the RF modulation in radians/sec, n is the effective index of refraction of the fiber, L is the length of the fiber optic delay time, c represents the speed of light in vacuum, $\tau$ is the fluorescence lifetime, and $\Phi$ is the sum of all discrete phase shifts in the loop (except for those associated with the fluorophore). Most importantly, $\Phi$ includes the phase shift from the electronic phase shifter. Assuming that $\tau$ is constant during the measurements, one may take the derivative of Eq. 4 to obtain $$\frac{d\Phi}{d\Omega} = -\left[\left(\frac{nl}{c}\right) + \frac{\tau}{1+(\Omega\tau)^2}\right] \quad (5)$$

Collecting terms in powers of $\tau$, Eq. 5 may be rewritten as $$\Omega^2\left(\frac{d\Phi}{d\Omega} + \left(\frac{nl}{c}\right)\right)\tau^2 + (1)\tau + \left(\frac{d\Phi}{d\Omega} + \left(\frac{nl}{c}\right)\right) = 0 \quad (6)$$

Using the quadratic formula, Eq. 6 can be solved for $\tau$, with the resulting formula $$\tau = \frac{-1 \pm \sqrt{1 - 4\Omega^2\left(\frac{d\Phi}{d\Omega} + \left(\frac{nl}{c}\right)\right)^2}}{2\Omega^2\left(\frac{d\Phi}{d\Omega} + \left(\frac{nl}{c}\right)\right)} \quad (7)$$

The choice of the ± sign in Eq. 7 requires some understanding of the role that the square root term plays. If the square root term is neglected, Eq. 7 returns a value of $\tau \approx 1/\Omega$. Hence, if the system is operated in the regime $\Omega\tau<1$, + must be selected. If the system is operated in the regime $\Omega\tau>1$, − must be selected.

The important variable in Eq. 7 is $d\Phi/d\Omega$. The phase shift $d\Phi$ may be created by applying a known control voltage to a phase shifter in the loop. This would result in a known value of dΦ, determined from the calibration curve of the phase shifter's output versus control voltage. The resulting frequency shift dΩ may be measured with a frequency counter.

If one had infinite precision and no error in the quantities dΦ and dΩ, Eq. 7 could be used to determine τ over a wide range of operational frequencies Ω. However, this is not the case in reality. It is possible to determine the error limits of this technique. Taking a partial derivative of Eq. 5 with respect to lifetime yields $$\frac{\partial}{\partial \tau}\left(\frac{d\Phi}{d\Omega}\right) = -\left[\frac{1-(\Omega\tau)^2}{(1+(\Omega\tau)^2)^2}\right] \quad (8)$$

Eq. 8 can be reorganized to predict the uncertainty levels in τ:

$$\delta\tau = -\left[\frac{(1+(\Omega\tau)^2)^2}{(1-(\Omega\tau)^2)}\right]\delta\left(\frac{d\Phi}{d\Omega}\right) \quad (9)$$

Which, in turn, can be rewritten as, $$\delta\tau = \left[\frac{(1+(\Omega\tau)^2)^2}{(1-(\Omega\tau)^2)}\right]\left[\left(\frac{nl}{c}\right)+\frac{\tau}{1+(\Omega\tau)^2}\right]\left[\frac{\delta\left(\frac{d\Phi}{d\Omega}\right)}{\left(\frac{d\Phi}{d\Omega}\right)}\right] \quad (10)$$

Which may be further simplified by assuming that (nl/c)≈(2π/Ω), allowing a final form:

$$\left[\frac{\delta\tau}{\tau}\right] = \left\{\left[\frac{(1+(\Omega\tau)^2)}{(1-(\Omega\tau)^2)}\right]\left[\frac{2\pi(1+(\Omega\tau)^2)}{\Omega\tau}+\frac{1}{1-(\Omega\tau)^2}\right]\right\}\left[\frac{\delta\left(\frac{d\Phi}{d\Omega}\right)}{\left(\frac{d\Phi}{d\Omega}\right)}\right] \quad (11)$$

Eq. 11 relates the fractional errors in lifetime to the fractional error in dΦ/dΩ, which is given by $$\left[\frac{\delta\left(\frac{d\Phi}{d\Omega}\right)}{\left(\frac{d\phi}{d\Omega}\right)}\right] = \sqrt{\left[\frac{\delta(d\Phi)}{d\Phi}\right]^2+\left[\frac{\delta(d\Omega)}{d\Omega}\right]^2} \quad (12)$$

Figure 5:
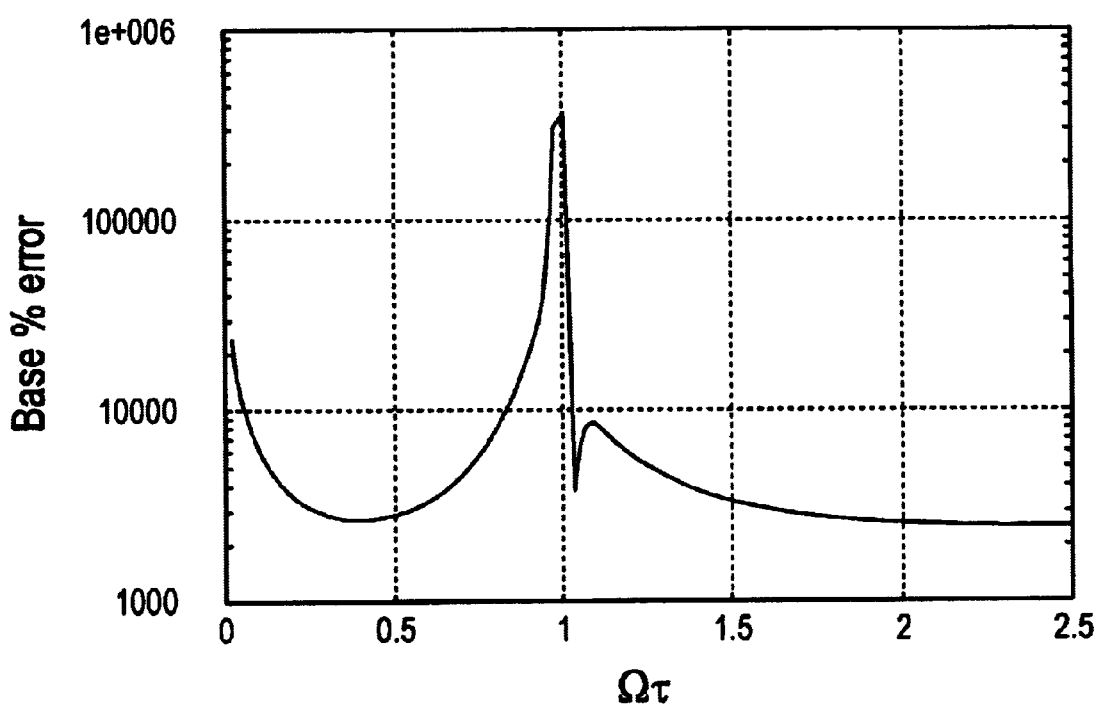
FIG. 5 is a plot of the base percent error versus $\Omega\tau$ for the embodiment of FIG. 3; the true percent error is the base percent error multiplied by the fractional error of $d\Phi/d\Omega$.

A plot of the braced part of Eq. 11 versus Ωτ is shown in FIG. 5. This part of the equation may be considered the "base fractional error" inherent in the technique. This base value, multiplied by the fractional error of dΦ/dΩ given by Eq. 12, would provide the uncertainty levels of an absolute lifetime measurement. Examination of FIG. 5 shows two unfortunate facts, however. First, the base error in the vicinity of Ωτ≈1 is enormous. This means that the same closed loop system cannot be used for the high precision relative measurements demonstrated above and this modified technique due to fiber length and amplifier center band frequency differences. Second, the base error at best is around 2500% (near Ωτ≈0.4 and Ωτ≈2.4). This means that even if the percent error in the measurements of both dΦ and dΩ were less than 1%, the uncertainty in lifetime of τ would be on the order of 35%. In order to compensate for this, numerous measurements would be needed so that the uncertainty of the average would be within acceptable parameters.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A fluorescence average excited-state lifetime sensor comprising:
   a fluorescence excitation light source;
   means for directing light from said light source to a sample;
   means for receiving fluorescence light generated by the sample; and
   a narrow-band resonance amplifier providing gain necessary to support self-oscillations in an opto-electronic loop comprising said light source, the sample, said directing means, said receiving means, and said resonance amplifier.

2. The sensor of claim 1 wherein light from said light source and said fluorescence light have different wavelengths and each carry a radio frequency intensity modulation in said loop.

3. The sensor of claim 1 wherein said light source comprises a light emitting diode.

4. The sensor of claim 3 wherein said light source comprises a blue light emitting diode.

5. The sensor of claim 1 wherein said receiving means comprises a long-wavelength-pass optical filter to prevent reception of light from said light source.

6. The sensor of claim 1 wherein said directing means directs light to a plurality of fluorophores.

7. The sensor of claim 6 wherein said receiving means receives light with radio frequency intensity modulation of identical frequency as that of said light source but phase shifted.

8. The sensor of claim 1 wherein said receiving means comprises a photomultiplier tube.

9. The sensor of claim 8 wherein said receiving means is connected to an input of said resonance amplifier.

10. The sensor of claim 1 wherein said amplifier comprises a resonance radio frequency amplifier.

11. The sensor of claim 10 wherein a central frequency of said amplifier and lengths of said directing and receiving means are such that an RF modulation frequency multiplied by an excited-state fluorescence lifetime of fluorophores in said sample is approximately one.

12. The sensor of claim 1 additionally comprising a frequency counter receiving a signal between said amplifier and said light source.

13. The sensor of claim 12 additionally comprising a second light source and a photodetector receiving output from said second light source and providing input to said frequency counter.

14. The sensor of claim 1 wherein said light source is a diode laser.

15. The sensor of claim 14 wherein said light source is a diode laser selected from the group consisting of blue and red diode lasers.

16. The sensor of claim 1 wherein said resonance amplifier prevents higher order oscillations.

17. The sensor of claim 1 additionally comprising an electronic phase shifter within said opto-electronic loop and also comprising a second opto-electronic loop comprising said electronic phase shifter, a second means for receiving fluorescence light generated by the sample, and a phase detector.

18. The sensor of claim 17 wherein the light from said light source is used as a light carrier of radio frequency intensity modulation in said opto-electronic loop.

19. The sensor of claim 17 wherein the fluorescence light is used as a light carrier of radio frequency intensity modulation in said second opto-electronic loop.

20. The sensor of claim 1 having a sub-picosecond resolution for changes in average excited-state lifetime of the sample.

21. The sensor of claim 1 wherein said sensor permits measurements of changes of chemical environment when the sample exhibits changes of fluorescence average excited-state lifetime in response to changes of the chemical environment.

22. The sensor of claim 1 wherein said sensor permits measurements of changes of physical environment when the sample exhibits changes of fluorescence average excited-state lifetime in response to changes of the physical environment.

23. The sensor of claim 1 wherein said sensor permits measurements of changes of concentration of one or more chemical species when the sample exhibits changes of fluorescence average excited-state lifetime in response to changes of concentration of the chemical species.

24. The sensor of claim 1 wherein said sensor permits measurements of changes of concentration of one or more biological species when the sample exhibits changes of fluorescence average excited-state lifetime in response to changes of concentration of the biological species.

25. A fluorescence average absolute lifetime sensor comprising:
   a fluorescence excitation light source;
   means for directing light from the light source to a sample;
   means for receiving fluorescence light generated by the sample;
   an electronic phase shifter; and
   a narrow-band resonance amplifier providing gain necessary to support self-oscillations in an opto-electronic loop comprising said light source, the sample, said directing means, said receiving means, said phase shifter, and said resonance amplifier.

26. The sensor of claim 25 wherein light from said light source and said fluorescence light have different wavelengths and each carry a radio frequency intensity modulation in said loop.

27. The sensor of claim 25 wherein said amplifier comprises a resonance radio frequency amplifier.

28. The sensor of claim 27 wherein a central frequency of said amplifier and lengths of said directing and receiving means are such that an RF modulation frequency multiplied by an excited-state fluorescence lifetime of fluorophores in said sample is not approximately one.

29. The sensor of claim 25 wherein said directing means directs light to a plurality of fluorophores.

30. The sensor of claim 29 wherein said receiving means receives light with radio frequency intensity modulation of identical frequency as that of said light source but phase shifted.

31. A fluorescence average excited-state lifetime sensing method comprising the steps of:
   exciting a fluorescence excitation light source;
   directing light from the light source to a sample;
   receiving fluorescence light generated by the sample; and
   providing narrow-band resonance amplification providing gain necessary to support self-oscillations in an opto-electronic loop comprising the light source, the sample, light directing means, light receiving means, and resonance amplification means.

32. The method of claim 31 wherein in the directing and receiving steps light from the light source and the fluorescence light have different wavelengths and each carry a radio frequency intensity modulation in the loop.

33. The method of claim 31 wherein in the exciting step the light source comprises a light emitting diode.

34. The method of claim 33 wherein in the exciting step the light source comprises a blue light emitting diode.

35. The method of claim 31 wherein the receiving step comprises employing a long-wavelength-pass optical filter to prevent reception of light from the light source.

36. The method of claim 31 wherein the directing step directs light to a plurality of fluorophores.

37. The method of claim 36 wherein the receiving step receives light with radio frequency intensity modulation of identical frequency as that of the light source but phase shifted.

38. The method of claim 31 wherein the receiving step comprises employing a photodetector.

39. The method of claim 38 wherein the receiving step comprises employing a photomultiplier tube.

40. The method of claim 39 wherein in the receiving and providing steps the photodetector is connected to an input of the resonance amplification means.

41. The method of claim 31 wherein the providing step comprises employing a resonance radio frequency amplifier.

42. The method of claim 41 wherein in the providing step a central frequency of the amplifier and lengths of the light directing and receiving means are such that an RF modulation frequency multiplied by an excited-state fluorescence lifetime of fluorophores in the sample is approximately one.

43. The method of claim 31 additionally comprising the step of employing a frequency counter receiving a signal between the amplifier and the light source.

44. The method of claim 43 additionally comprising the step of employing a second light source and a photodetector receiving output from the second light source and providing input to the frequency counter.

45. The method of claim 31 wherein in the exciting step the light source is a diode laser.

46. The method of claim 45 wherein in the exciting step the light source is a diode laser selected from the group consisting of blue and red diode lasers.

47. The method of claim 31 wherein in the providing step the resonance amplification prevents higher order oscillations.

48. The method of claim 31 additionally comprising the step of employing an electronic phase shifter within the opto-electronic loop and also employing a second opto-electronic loop comprising the electronic phase shifter, a second means for receiving fluorescence light generated by the sample, and a phase detector.

49. The method of claim 31 wherein the method provides a sub-picosecond resolution for changes in average excited-state lifetime of the sample.

50. The method of claim 31 additionally comprising the step of measuring changes of chemical environment when the sample exhibits changes of fluorescence average excited-state lifetime in response to changes of the chemical environment.

51. The method of claim 31 additionally comprising the step of measuring changes of physical environment when the sample exhibits changes of fluorescence average excited-state lifetime in response to changes of the physical environment.

52. The method of claim 31 additionally comprising the step of measuring changes of concentration of one or more chemical species when the sample exhibits changes of fluorescence average excited-state lifetime in response to changes of concentration of the chemical species.

53. The method of claim 31 additionally comprising the step of measuring changes of concentration of one or more biological species when the sample exhibits changes of fluorescence average excited-state lifetime in response to changes of concentration of the biological species.

54. The method of claim 31 additionally comprising the step of obtaining directly information regarding changes of concentration in a species selected from the group consisting of chemical and biological species from measurement of self-oscillation frequency in the opto-electronic loop.

55. A fluorescence average absolute lifetime sensing method comprising the steps of:

exciting a fluorescence excitation light source;

directing light from the light source to a sample;

receiving fluorescence light generated by the sample;

employing an electronic phase shifter; and providing narrow-band resonance amplification providing gain necessary to support self-oscillations in an opto-electronic loop comprising the light source, the sample, light directing means, light receiving means, the phase shifter, and resonance amplification means.

56. The method of claim 55 wherein the providing step comprises employing a resonance radio frequency amplifier.

57. The method of claim 56 wherein in the providing step a central frequency of the amplifier and lengths of the light directing and receiving means are such that an RF modulation frequency multiplied by an excited-state fluorescence lifetime of fluorophores in the sample is not approximately one.

58. The method of claim 55 wherein the directing step directs light to a plurality of fluorophores.

59. The method of claim 58 wherein the receiving step receives light with radio frequency intensity modulation of identical frequency as that of the light source but phase shifted.

* * * * *